United States Patent [19]
Fiore et al.

[11] Patent Number: 5,156,618
[45] Date of Patent: Oct. 20, 1992

[54] LASER MIST EVACUATOR ATTACHMENT

[76] Inventors: Nello Fiore, 4945 Carlyn Dr.; Fred Fiore, 60 Clover Dr., both of Pittsburgh, Pa. 15236

[21] Appl. No.: 797,197

[22] Filed: Nov. 25, 1991

[51] Int. Cl.⁵ .............................................. A61M 1/00
[52] U.S. Cl. .................................. 604/315; 604/317; 604/902
[58] Field of Search ............... 604/315, 317, 319, 902; 239/561, 565, 545, 544, 543

[56] References Cited

U.S. PATENT DOCUMENTS

| | | | |
|---|---|---|---|
| 4,419,301 | 12/1983 | Nahra et al. ..................... | 239/561 X |
| 4,836,702 | 6/1989 | Allen .............................. | 239/543 X |
| 4,921,492 | 5/1990 | Schultz et al. ..................... | 604/315 |
| 4,927,083 | 5/1990 | Daunt .............................. | 239/561 X |
| 4,963,134 | 10/1990 | Backscheider et al. ............ | 604/319 |
| 5,015,243 | 5/1991 | Schifano ............................. | 604/315 |
| 5,047,072 | 9/1991 | Wertz et al. ..................... | 604/319 X |

*Primary Examiner*—Randall L. Green
*Assistant Examiner*—Dinh X. Nguyen
*Attorney, Agent, or Firm*—William J. Ruano

[57] ABSTRACT

A laser mist evacuator attachment comprising a stubby U-shaped vacuum nozzle having a substantially inverted V-shaped tube with extremities connected to the extremities of the stubby U-shaped nozzle together with a plurality of holes in confronting relationship in the tube for drawing in a vacuum mist. The tube is preferably provided with a flexible backing sheet which is curved to fit the body of the patient and the rear of which is coated with adhesive material.

2 Claims, 2 Drawing Sheets

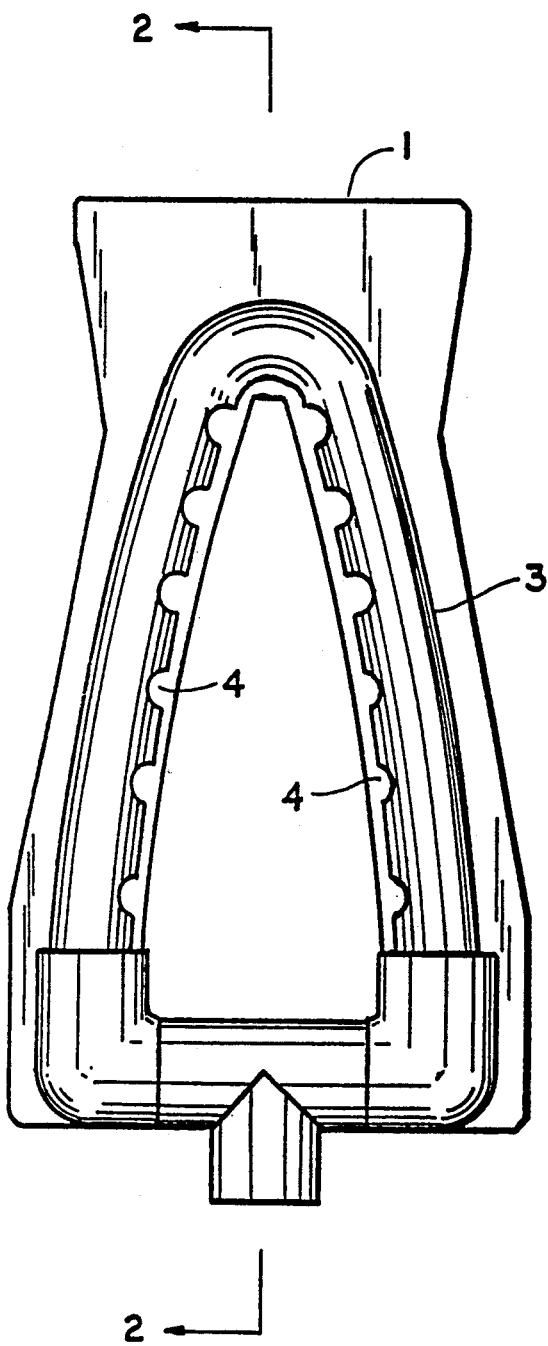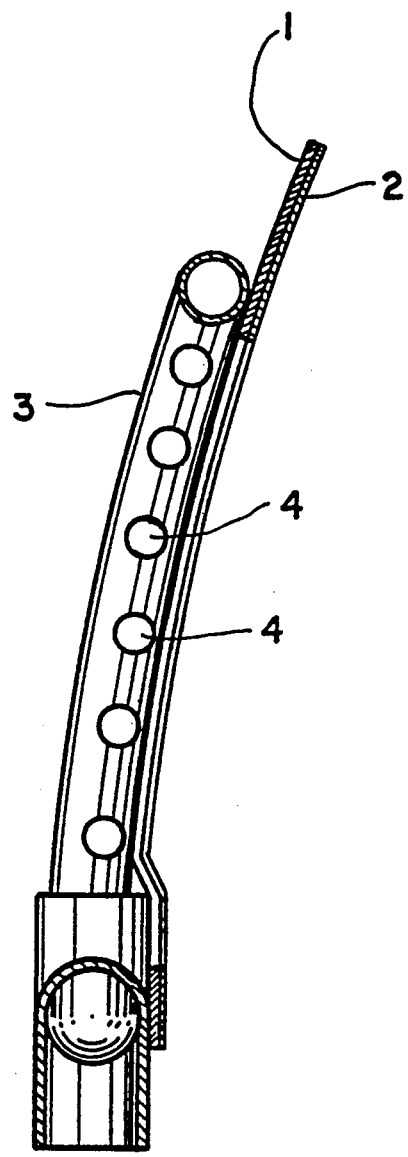
FIG. 1
FIG. 2

LASER MIST EVACUATOR ATTACHMENT

BACKGROUND OF THE INVENTION

In surgery performed in the operating room or doctor's office, a vacuum device is used for the removal of the plume or laser mist generated during a process in which a laser beam or cauterization technique is necessary.

In the past, a vacuum pump was directed to the vaginal or rectal area for the removal of the plume or laser mist. However, problems have arisen by the escape of said laser mist causing obscurity of the surgical area viewed by the operating doctor as well as rise of such plume or laser mist in the nostrils of the doctor performing laser surgery resulting in the causing of irritation, sometimes developing in a venerial wart in his nasal passages.

SUMMARY OF THE INVENTION

An object of the present invention is to provide an evacuator attachment for surrounding the vaginal or rectal area or any other area on the patient while laser surgery or cauterization is being performed.

BRIEF DESCRIPTION OF THE DRAWINGS

FIG. 1 shows a plan view of the laser mist evacuator attachment embodying the present invention;

FIG. 2 shows a section taken along line 2—2 of FIG. 1;

DESCRIPTION OF THE PREFERRED EMBODIMENTS

Figure 3:
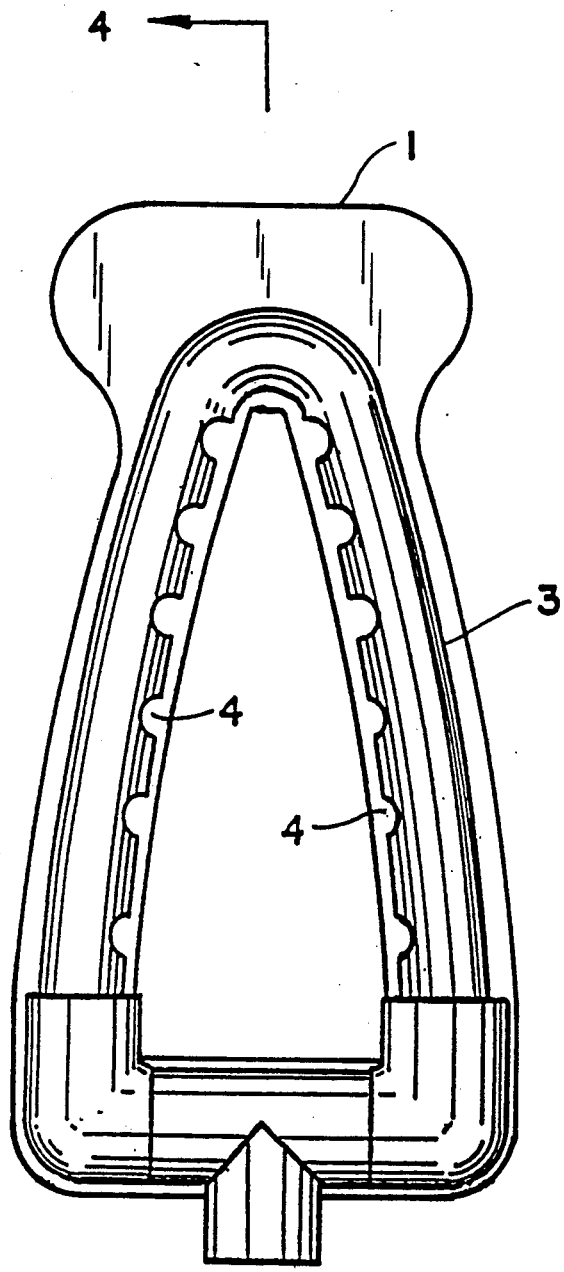
FIG. 3 shows a plan view of a modification.

Referring to FIGS. 1 and 2, numeral 1 denotes a pliable or rigid material, such as pliable or rigid plastic material provided with or without an adhesive backing or coating 2 of any suitable adhesive material unaffected by moisture, such as used for dentures, which will adhere to wet draping which surrounds the area where laser surgery is being performed. An example is an adhesive having the name RIGIDENT DENTURE ADHESIVE CREAM manufactured by Carter Products Division of Carter-Wallace, Inc. or other denture adhesives.

To ensure the attachment is held in the proper position, the top of the adhesive backing may be made of whatever size is necessary. For example, it may be designed and fabricated 4" wide and extend 12" from the pointed tip of the tubing.

Attached to backing 1 is a somewhat inverted V-shaped tube 3 also of the same material as backing 1, such as a plastic material, having a plurality of holes 4 of the same size formed along the inner side of the tubing 3, which holes are spaced, but the spacing becomes less in the upward direction of the tubing 3, for example, holes of a diameter of 5/16" may be used having a ½" spacing at the base which becomes progressively smaller to ¼" spacing at the top. The reason for this is to provide a greater vacuum area adjacent the top of tube 3 because of the tendency of the vacuum mist to rise. Instead of having the holes in exact confronting relationship they are preferably moved slightly to the right towards the surgical surface as shown in the lower holes in FIG. 2. This aids in removal of the odor-causing mist that other wise might escape.

Figure 4:
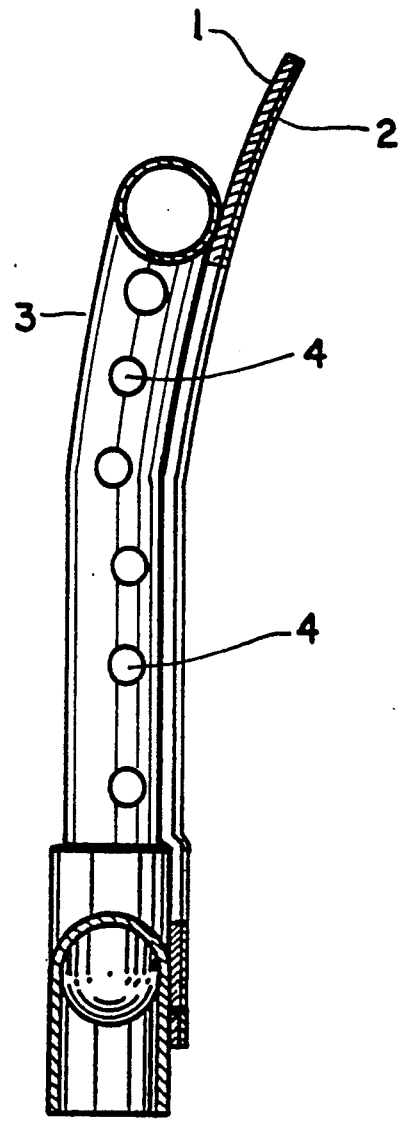
FIG. 4 shows a section taken along line 4—4 of FIG. 3.

FIGS. 3 and 4 shows a construction substantially the same as FIGS. 1 and 2 except making the lower portion almost vertical and only the top portion bent. The backing 1 does not extend outwardly to the extent of that shown in FIGS. 1 and 2.

In some instances, the perimeter of the tube 3 may be more of an inverted U-shape or even of a somewhat elliptical or circular shape with the vacuum being drawn in one end thereof.

While we have illustrated and described several embodiments of our invention, it will be understood that these are by way of illustration only and that various changes and modifications are contemplated in our invention within the scope of the following claims:

I claim:

1. A laser mist evacuator attachment comprising:
    (a) a curved backing having a central opening and an angled surface contouring to a part of the body of a patient having laser surgery having an adhesive layer attached to the angled surface;
    (b) a stubby U-shaped nozzle having opposite-ended extremities attached to said backing and having a central opening connected to a source of vacuum, also having an opening at each extremity of said stubby U-shape;
    (c) a flexible tube of substantially inverted V shape mounted on said backing, surrounding said central opening, and having extremities thereof connected to said extremity openings of said stubby U-shape;
    (d) a plurality of spaced openings formed in confronting relationship on said flexible tube for evacuating laser mist developed in said operating site.

2. A laser mist evacuator attachment as recited in claim 1 wherein said plurality of spaced openings become progressively closer in a direction opposite of the extremities of said tube.

* * * * *